(12) United States Patent
Lee et al.

(10) Patent No.: US 10,578,492 B2
(45) Date of Patent: Mar. 3, 2020

(54) POLARIMETER FOR DETECTING POLARIZATION ROTATION

(71) Applicants: SAMSUNG ELECTRONICS CO., LTD., Suwon-si (KR); CALIFORNIA INSTITUTE OF TECHNOLOGY, Pasadena, CA (US)

(72) Inventors: Duhyun Lee, Yongin-si (KR); Andrei Faraon, Pasadena, CA (US); Ehsan Arbabi, Pasadena, CA (US); Sadegh Faraji-Dana, Pasadena, CA (US); Mahsa Seyedeh Kamali, Pasadena, CA (US); Yu Horie, Pasadena, CA (US); Chanwook Baik, Yongin-si (KR)

(73) Assignees: SAMSUNG ELECTRONICS CO., LTD., Suwon-si (KR); CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 16/146,523

(22) Filed: Sep. 28, 2018

(65) Prior Publication Data

US 2019/0101448 A1 Apr. 4, 2019

Related U.S. Application Data

(60) Provisional application No. 62/565,603, filed on Sep. 29, 2017.

(30) Foreign Application Priority Data

Nov. 20, 2017 (KR) .................. 10-2017-0154982

(51) Int. Cl.
*G01J 4/04* (2006.01)
(52) U.S. Cl.
CPC .................... *G01J 4/04* (2013.01)

(58) Field of Classification Search
CPC ........................................... G01J 4/04
(Continued)

(56) References Cited

U.S. PATENT DOCUMENTS 6,327,037 B1 * 12/2001 Chou ..................... G01J 4/04
356/484
6,927,853 B2 * 8/2005 Geiler ..................... G01L 1/24
356/33

(Continued)

FOREIGN PATENT DOCUMENTS

JP 6057606 B2 1/2017

OTHER PUBLICATIONS

Zhao et al. ("Optical polarization beam splitting through anisotropic metamaterial slab realized by layered metal-dielectric system", 2007 Asia Optical Fiber Comunication and Optoelectronics Conference) (Year: 2007).*

(Continued)

*Primary Examiner* — Hina F Ayub
(74) *Attorney, Agent, or Firm* — Sughrue Mion, PLLC

(57) ABSTRACT

A polarimeter for measuring a polarization rotation caused by a measurement object is provided, the polarimeter including an optically active material. The polarimeter includes a light source unit for irradiating a measurement object with light having a specific polarization; an anisotropic meta surface element for splitting reaction light, obtained by reacting the light of the specific polarization irradiated by the light source unit with the measurement object, into first and second reaction light; and a detection unit for detecting the first and second reaction light separated by the anisotropic meta surface element according to polarization. The polarization rotation caused by the measurement object may be calculated by comparing detection signals of the first and second reaction light detected by the detection unit.

18 Claims, 7 Drawing Sheets

(58) Field of Classification Search
USPC .......................................................... 356/367
See application file for complete search history.

(56) References Cited

U.S. PATENT DOCUMENTS

| | | | |
|---|---|---|---|
| 7,245,952 B2 | 7/2007 | Cameron | |
| 8,718,734 B2 | 5/2014 | Cameron | |
| 9,116,302 B2 | 8/2015 | McCarthy et al. | |
| 2003/0223064 A1* | 12/2003 | Anderson | A61B 3/1005 356/364 |
| 2005/0018290 A1* | 1/2005 | Kiss | G02B 27/288 359/485.02 |
| 2006/0193044 A1* | 8/2006 | Blum | G01J 4/04 359/485.01 |
| 2007/0146632 A1* | 6/2007 | Chipman | A61B 3/12 351/205 |
| 2009/0231583 A1* | 9/2009 | Smith | G01J 4/04 356/367 |
| 2010/0259759 A1* | 10/2010 | Goldberg | G01J 4/04 356/487 |
| 2011/0261441 A1* | 10/2011 | Zheludev | G02B 1/005 359/352 |
| 2014/0152988 A1* | 6/2014 | Liu | A61B 5/14532 356/364 |
| 2015/0002791 A1* | 1/2015 | Nam | G02B 5/3058 349/96 |
| 2016/0341859 A1 | 11/2016 | Shvets et al. | |
| 2017/0351017 A1* | 12/2017 | Cui | G02B 5/3058 |
| 2018/0307132 A1* | 10/2018 | Zhang | G03F 1/26 |

OTHER PUBLICATIONS

Arbabi et al., "Dielectric Metasurfaces for Complete Control of Phase and Polarization with Subwavelength Spatial Resolution and High Transmission", Nature Nanotechnology, Aug. 3, 2015, 27 pages.

* cited by examiner

POLARIMETER FOR DETECTING POLARIZATION ROTATION

CROSS-REFERENCE TO RELATED APPLICATION(S)

This application is based on and claims the benefit of U.S. Provisional Application No. 62/565,603, filed on Sep. 29, 2017, in the US Patent and Trademark Office and claims priority, under 35 U.S.C. § 119, to Korean Patent Application No. 10-2017-0154982, filed on Nov. 20, 2017, in the Korean Intellectual Property Office, the disclosures of which are incorporated by reference herein in their entireties.

BACKGROUND

1. Field

Apparatuses consistent with example embodiments relate to a polarimeter, and more particularly, to a polarimeter for detecting a polarization rotation by using an optically active material.

2. Description of the Related Art

A polarimeter may be used to determine a concentration of an optically active material such as steroids, amino acids, vitamins, polymers, sugars, and the like, in a sample. When a polarimeter is used, a rotation angle of polarized light passing through the optically active material may be measured. However, a polarization rotation of the polarized light, due to the optically active material is often not be large enough to be easily detected. Therefore, an additional device such as a Faraday rotator is often needed to increase the rotation angle measurement sensitivity by using the optically active material. Alternatively, a longer reaction length may be used to obtain a sufficient polarization rotation. This approach, however, makes a system complex and bulky.

SUMMARY

One or more example embodiments may provide a polarimeter in which a rotation angle measurement sensitivity of polarized light passing through an optically active material is high and a form factor is improved.

One or more example aspects and advantages will be set forth in part in the description which follows and, in part, will be apparent from the description, or may be learned by practice of the presented example embodiments.

In accordance with an aspect of an example embodiment, a polarimeter includes a light source unit configured to irradiate light of a specific polarization onto a measurement object including an optically active material; an anisotropic meta surface element configured to split reaction light, obtained by reacting the light of the specific polarization irradiated from the light source unit with the measurement object, into first and second reaction light according to polarization; a detection unit configured to detect the first and second reaction light separated by the anisotropic meta surface element according to polarization; and a determination unit configured to calculate a rotation angle of the polarization caused by the measurement object by comparing detection signals of the first and second reaction light detected by the detection unit.

The anisotropic meta surface element may split the reaction light into the first reaction light of a first polarization and the second reaction light of a second polarization orthogonal to the first reaction light.

The specific polarization may be the same as one of the first polarization and the second polarization.

The first polarization and the second polarization may be linear polarizations orthogonal to each other.

The anisotropic meta surface element may be a phase mask having a sub wavelength structure.

The anisotropic meta surface element may include a low refractive index dielectric substrate and an array of high refractive index three dimensional shapes, having sub wavelength structures, disposed on the low refractive index dielectric substrate.

A polarization reaction of incident light to the anisotropic meta surface element may be determined based on a size difference between two axes of each of the high refractive index dielectric three-dimensional shapes.

The anisotropic meta surface element may be located on a light-receiving surface of the detection unit.

The light source unit may include a light source configured to emit light and a polarizer configured to polarize the light emitted from the light source unit and output the light of the specific polarization, and only the light of the specific polarization may be irradiated to the measurement object.

The polarizer may include a meta surface polarizer.

The meta surface polarizer may include a low refractive index dielectric substrate and an array of high refractive index dielectric three dimensional shapes, having sub wavelength structures, disposed on the substrate.

A reaction of the polarization of incident light to the meta surface polarizer may be determined by a size difference between two axes of each of the high refractive index dielectric three-dimensional shapes.

The specific polarization may be a linear polarization.

The detection unit may include a plurality of detectors, each configured to detect one of the first reaction light and the second reaction light.

Each of the plurality of detectors may include one of a photodiode, a PMT detector, a photodiode linear array, and an image sensor.

The detection unit may include a single detector, the single detector including one of a photodiode linear array and an image sensor.

The polarimeter may further include a spectrometer configured to measure light scattered from the measurement object.

The measurement object may include an optically active material.

BRIEF DESCRIPTION OF THE DRAWINGS

These and/or other example aspects and advantages will become apparent and more readily appreciated from the following description of example embodiments, taken in conjunction with the accompanying drawings in which.

DETAILED DESCRIPTION

Figure 1:
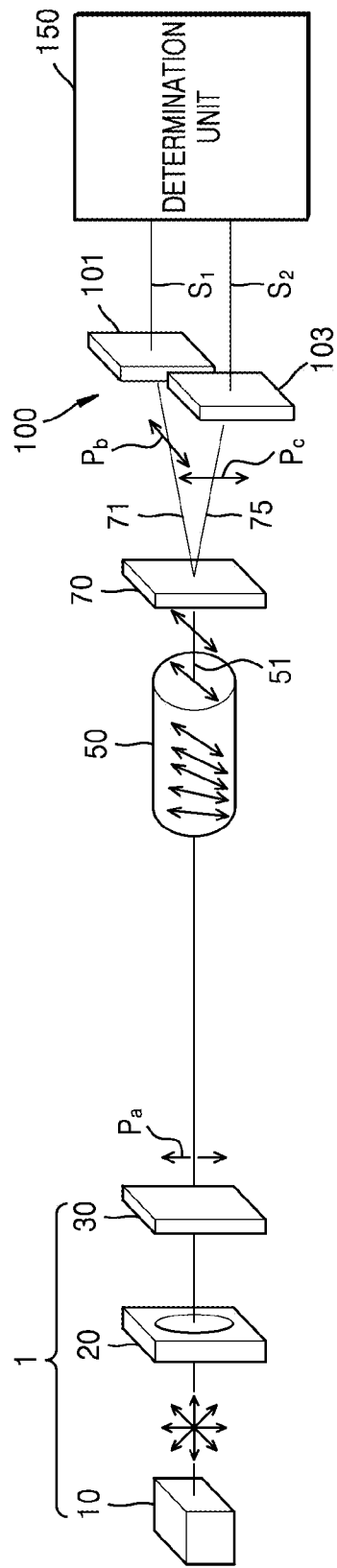
FIG. 1 schematically shows a configuration of a polarimeter according to an example embodiment.

Hereinafter, a polarimeter is described in detail with reference to the accompanying drawings. In the drawings, like reference numerals denote like elements, and the sizes or thicknesses of components may be exaggerated for convenience of description. The example embodiments described below are only illustrative, and various changes in form and details may be made therein.

FIG. 1 schematically shows a configuration of a polarimeter according to an example embodiment.

Referring to FIG. 1, the polarimeter includes a light source unit 1, an anisotropic meta surface element 70, a detection unit 100, and a determination unit 150. The light source unit 1 irradiates light of a specific polarization Pa toward a measurement object 50 including an optically active material. The anisotropic meta surface element 70 splits reaction light 51, obtained by the light of the specific polarization Pa emitted from the light source unit 1 reacting with the measurement object 50, into reaction light 71 and reaction light 75 according to polarization. The detection unit 100 detects the reaction light 71 and reaction light 75 obtained by splitting by the anisotropic meta surface element 70 according to the polarization. The determination unit 150 calculates a rotation angle of the polarization by the measurement object 50 by comparing detection signals of the reaction light 71 and the reaction light 75 detected by the detection unit 100. The determination unit may comprise a memory and a processor configured to execute software stored in the memory and thereby perform operations, as would be understood by one of skill in the art, on signals received from the detection unit.

The polarimeter according to the present example embodiment may obtain a characteristic of the measurement object 50 by measuring the polarization rotation by the measurement object 50. The measurement object 50 may include the optically active material. A polarization direction and an angle of incident light are influenced by a type and concentration of a material of the measurement object 50 including the optically active material, and thus the polarization rotation by the measurement object 50 may be measured using the polarimeter of the present example embodiment, thereby enabling a glucose analysis or a chemical analysis in food, beverages, and medicine fields. Further, the concentration of, for example, steroids, amino acids, vitamins, sugar and the like may be characterized by measuring the polarization rotation by the measurement object 50 using the polarimeter of the present example embodiment.

The light source unit 1 includes a light source 10 which emits light and a polarizer 30. The light source 10 emits light of a predetermined polarization. Here, the predetermined polarization may be arbitrary polarization. The predetermined polarization may be any one of a linear polarization, a circular polarization, and an elliptical polarization.

The polarizer 30 produces light of the specific polarization Pa with respect to the light emitted from the light source 10 such that only the light of the specific polarization Pa is irradiated onto the measurement object 50.

To this end, the polarizer 30 may include, for example, a meta surface polarizer. The meta surface polarizer is a phase mask having a sub-wavelength structure. The meta surface polarizer may include an array of high refractive index dielectric three-dimensional shapes, each having a sub wavelength structure, disposed on a low refractive index dielectric substrate. The high refractive index is higher than the low refractive index. The meta surface polarizer may control a reaction to polarization based on a size difference between two axes of the high refractive index dielectric three-dimensional shape. The meta surface polarizer may be arranged to emit light of, for example, linear polarization with respect to the light incident from the light source 10. Similar to the anisotropic meta surface element 70 described below, the meta surface polarizer may include elliptical posts, for example, as the high refractive index dielectric three-dimensional shapes, and an elliptical post array may be arranged such that light of, for example, a linear polarization is emitted, when the light incident from the light source 10 is incident thereon.

Alternately, instead of including a meta surface polarizer, the polarizer 30 may include a general polarizer that allows only light of the specific polarization Pa to pass therethrough, from the light incident from the light source 10

Alternately, the light source 10 itself may be configured to emit light of the specific polarization Pa to be irradiated onto the measurement object 50. In this case, the polarizer 30 may be omitted.

The light source unit 1 may further include a filter 20 between the light source 10 and the polarizer 30. The filter 20 may transmit only light of a wavelength band that provides good reactivity with the measurement object 50. The filter 20 may be omitted when the light source 10 itself emits only the light of the wavelength band that provides good reactivity with the measurement object 50.

According to the light source unit 1, described above, the light of the specific polarization Pa, for example light of a linear polarization, is output from the light source 10, transmitted through the polarizer 30, and is incident on the measurement object 50. The incident light reacts with the measurement object 50. The reaction light 51 is thereby output from the measurement object 50.

The reaction light 51 output due to the reaction between the light of the specific polarization Pa, emitted from the light source 10, with the measurement object 50, is split according to polarization into the reaction light 71 and the reaction light 75 by the anisotropic meta surface element 70.

Figure 2:
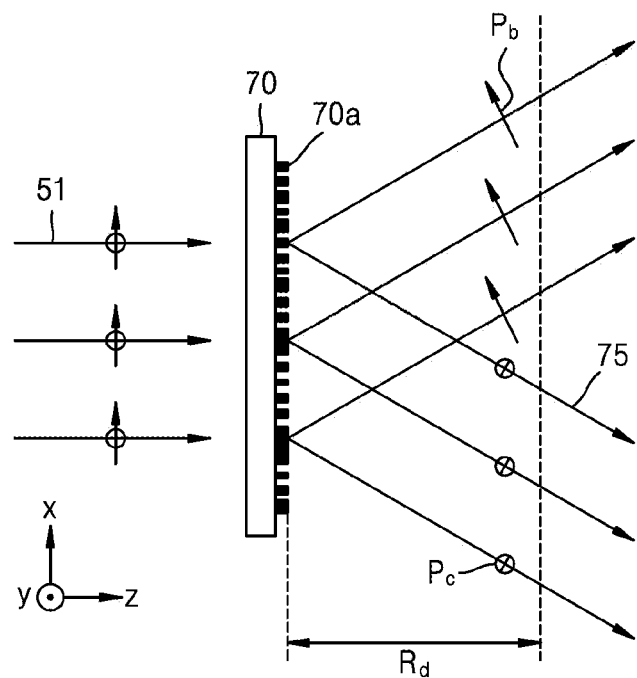
FIG. 2 illustrates a light path in which reaction light, incident from a measurement object, splits into first reaction light of a first polarization and second reaction light of a second polarization orthogonal thereto according to polarization by an anisotropic meta surface element of FIG. 1.

For example, as shown in FIG. 2, the anisotropic meta surface element 70 may split the reaction light 51, incident from the measurement object 50, into first reaction light 71 of a first polarization Pb and second reaction light 75 of a second polarization Pc orthogonal thereto. The first polarization Pb and the second polarization Pc may be linear polarizations orthogonal to each other. As exemplarily shown in FIG. 2, the first polarization Pb may be a horizontal linear polarization, and the second polarization Pc may be a vertical linear polarization. As another example, the first polarization Pb may be a vertical linear polarization, and the second polarization Pc may be a horizontal linear polarization.

As described above, the anisotropic meta surface element 70 may be a phase mask having sub wavelength structures to split the polarization light 51 into the first reaction light 71 of the first polarization Pb and the second reaction light 75 of the second polarization Pc, and may include a meta surface 70a having a large birefringence.

To this end, the anisotropic meta surface element 70 may be implemented as a phase mask having a sub wavelength structure, for example, by including an array of high refractive index dielectric three-dimensional shapes of sub wavelength structure on a low refractive index dielectric substrate. As the low refractive index dielectric substrate, for example, a silicon oxide substrate may be used. The high refractive index dielectric three-dimensional shapes may be formed of, for example, amorphous silicon.

A reaction of the reaction light 51 with the anisotropic meta surface element 70 may be controlled by controlling a size difference between the two axes of the high refractive index dielectric three-dimensional shapes.

Figure 3A:
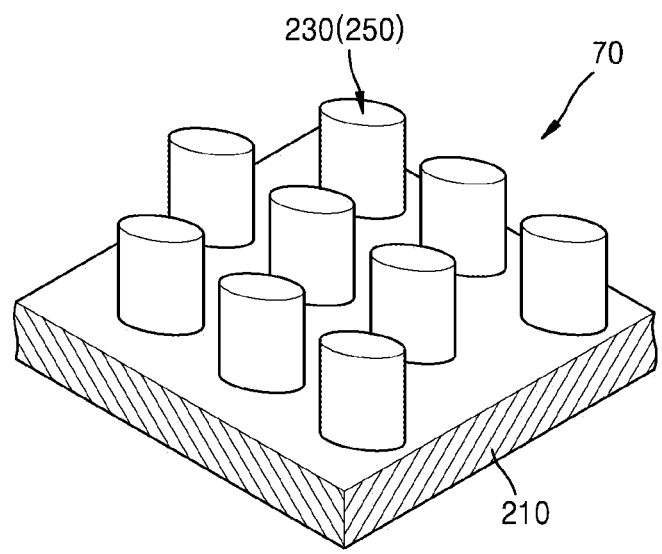
FIG. 3A is a schematic perspective view illustrating an example of an anisotropic meta surface element that may be applied to a polarimeter of FIG. 1.

For example, the anisotropic meta surface element 70 may include high refractive index dielectric three-dimensional shapes 230 which are elliptical posts 250, disposed in an array on a low refractive index dielectric substrate 210, as shown in FIG. 3A. The reaction of the reaction light 51 with anisotropic meta surface element 70 may be controlled by controlling a size difference between a major axis and a minor axis of an elliptical cross-section of the elliptical posts 250. The reaction of the reaction light 51 with the anisotropic meta surface element 70 may also be controlled according to an angle formed by the major axis of the elliptical cross-section of the elliptical posts 250 with a direction of the first polarization Pb of the first reaction light 71 or a direction of the second polarization Pc of the second reaction light 75. A silicon oxide substrate, for example, may be used as the low refractive index dielectric substrate 210. The high refractive index dielectric three-dimensional shapes 230 may be formed of, for example, amorphous silicon.

Figure 3B:
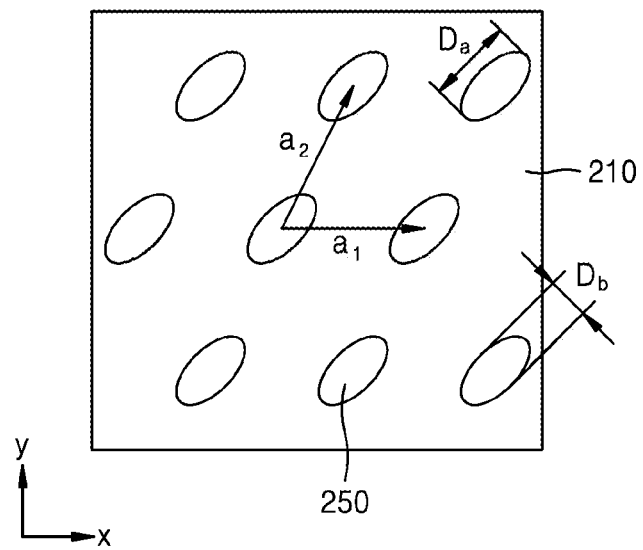
FIG. 3B is a plan view showing an array of high refractive index dielectric three-dimensional shapes of FIG. 3A.
Figure 3C:
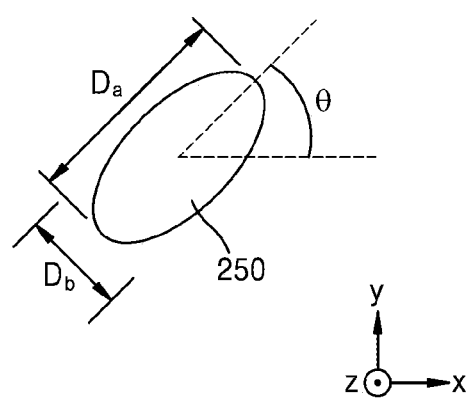
FIG. 3C is a plan view showing a high refractive index dielectric three-dimensional shape of FIG. 3A.

FIG. 3A schematically illustrates an example of the anisotropic meta surface element 70 that may be applied to a polarimeter of FIG. 1, wherein FIG. 3A is a perspective view illustrating the array of high refractive index dielectric three-dimensional shapes 230 included in the anisotropic meta surface element 70. FIG. 3B is a plan view showing the array of the high refractive index dielectric three-dimensional shapes 230 of FIG. 3A. FIG. 3C is a plan view showing a single high refractive index dielectric three-dimensional shape 230 of FIG. 3A.

Referring to FIGS. 3A to 3C, the high refractive index dielectric three-dimensional shapes 230 may be elliptical posts 250 formed on the low refractive index dielectric substrate 210. At this time, each elliptical post 250 may be formed in a sub wavelength scale such that the meta surface 70a as shown in FIG. 2 is formed by an array of the elliptical posts 250.

That is, the meta surface 70a of the anisotropic meta surface element 70 is configured as a sub wavelength artificial structure and may be an array of high refractive index dielectric three-dimensional shapes 230, each having a sub wavelength dimension, for example, an array of the elliptical posts 250. The term sub wavelength refers to a dimension smaller than a wavelength of the light to be incident thereon—i.e. the light to be polarized and split by the anisotropic meta surface element 70. At least one dimension of each of the high refractive index dielectric three-dimensional shapes 230 may be a sub wavelength dimension, for example, a dimension equal to or less than λ/2 when the wavelength of the light to be polarized and split by the anisotropic meta surface element 70 is λ. For example, when the high refractive index dielectric three-dimensional shapes 230 are the elliptical posts 250, at least one of a major axis diameter Da, a minor axis diameter Db, and spacing distances a1 and a2 of FIG. 3B between the elliptical posts 250 may be a sub wavelength dimension, for example, a dimension equal to or less than λ/2.

FIG. 3B is a plan view showing a part of an array of a high dielectric constant three-dimensional shapes forming the anisotropic meta surface element 70 and illustrates an example in which major axes of high dielectric constant three-dimensional shapes, that is, the elliptical posts 250, form a predetermined angle with respect to an x axis. To control a reaction of the incident light with the anisotropic meta surface element 70, the angle between a major axis direction of the ellipse of each of the elliptical posts 250 with the x axis may be controlled.

As shown in FIGS. 3B and 3C, when a diameter of the major axis of the elliptical cross-section of the elliptical posts 250 is denoted by Da and a diameter of a minor axis is denoted by Db, the reaction of the incident light with the anisotropic meta surface element 70 may be controlled by controlling a size difference between the diameter Da of the major axis and the diameter Db of the minor axis.

The reaction of the incident light with the anisotropic meta surface element 70 may be controlled by controlling an angle formed between the major axis of each elliptic post 250 forming a meta surface of the anisotropic meta surface element 70 and a direction of the first polarization Pb of the first reaction light 71 and a direction of the first polarization Pb of the second reaction light 75.

For example, as shown in FIG. 2, when the direction of the first polarization Pb is on an x-z plane and the direction of the second polarization Pb is parallel to the y-axis, the reaction of the incident light with the anisotropic meta surface element 70 may be controlled by controlling an angle θ formed by the major axis of each elliptic post 250 forming the meta surface of the anisotropic meta surface element 70 with the x axis. In FIG. 3C, the angle θ represents the angle formed by the major axis of the elliptical post 250 with the x axis.

Figure 4:
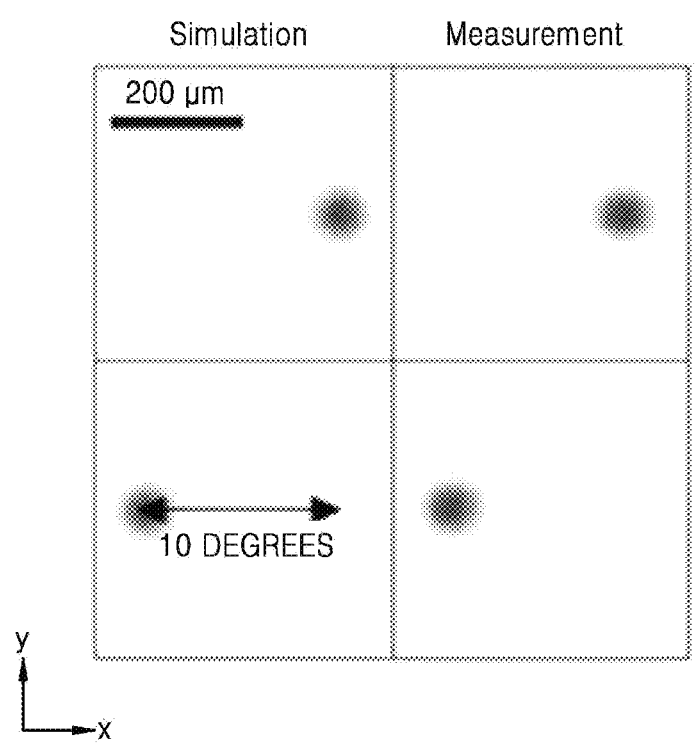
FIG. 4 illustrates that reaction light is received by splitting reaction light into first reaction light of a first polarization and second reaction light of a second polarization according to polarization by the anisotropic meta surface element of FIG. 2.

FIG. 4 illustrates a situation in which the reaction light 51 is received by splitting the reaction light 51 according to polarization into the first reaction light 71 of the first polarization Pb, for example, a horizontal linear polarization and the second reaction light 75 of the second polarization Pc, for example, a vertical linear polarization by the anisotropic meta surface element 70. FIG. 4 shows a comparison of a simulation result and an actual measurement when the anisotropic meta surface element 70 is designed to split the reaction light 51 into the first reaction light 71 and the second reaction light 75 at an angle of about 10 degrees and when the separated first reaction light 71 and second reaction light 75, is detected for example, at a distance Rd of about 1.5 mm.

As shown in FIG. 4, according to the anisotropic meta surface device 70 of an example embodiment, the incident reaction light 51 may be split according to polarization into the first reaction light 71 of the horizontal linear polarization and the second reaction light 75 of the vertical linear polarization, and a result may be obtained that the simulation result and the actual measurement are similar to each other.

According to the polarimeter to which the anisotropic meta surface element 70 is applied, since a meta surface may be formed on a flat surface to have a high birefringence, the polarimeter may be implemented in a small size.

The specific polarization Pa of light radiated from the light source unit 1 to the measurement object 50 may be the same as any one of the first polarization Pb and the second polarization Pc of the first reaction light 71 and the second reaction light 75, respectively. For example, when the first polarization Pb and the second polarization Pc are linear polarizations orthogonal to each other, the specific polarization Pa may be one of the first polarization Pb and the second polarization Pc. FIGS. 1 and 2 illustrate an example in which the specific polarization Pa is a vertical linear polarization, the first polarization Pb of the first reaction light 71 is a horizontal linear polarization, and the second polarization Pc of the second reaction light 75 is the vertical linear polarization. As another example, the specific polarization Pa may be the horizontal linear polarization, and one of the first polarization Pb and the second polarization Pc may be the vertical linear polarization, and the other one may be the horizontal linear polarization. As another example, the specific polarization Pa may be, for example, one circular polarization, and one of the first polarization Pb and the second polarization Pc may be the one circular polarization, and the other one may be another orthogonal circular polarization.

Referring again to FIG. 1, the detection unit 100 may include a plurality of detectors each detecting on of the reaction light 71 and the reaction light 75, having been separated according to polarization by the anisotropic meta surface element 70. The plurality of detectors may include, for example, a photodiode, a photodiode linear array, a PMT detector or an image sensor.

For example, the detection unit 100 may include a first detector 101 detecting the first reaction light 71 of the first polarization Pb and a second detector 103 detecting the second reaction light 75 of the second polarization Pc. The first reaction light 71 and the second reaction light 75 may be split by the anisotropic meta surface element 70 to form a predetermined angle with each other, and thus the first reaction light 71 and the second reaction light 75 may be incident on the detection unit 100 at different incident angles.

The first detector 101 and the second detector 103 may each include a point detector or a region detector. For example, at least one of the first detector 101 and the second detector 103 may include a photodiode, a photo multiplier tube (PMT) detector, a photodiode linear array, or an image sensor. The photodiode and the PMT detector may correspond to point detectors. The photodiode linear array and the image sensor correspond to region detectors.

Detection signals of the reaction light 71 and the reaction light 75 detected by the detection unit 100 are compared in the determination unit 150. The determination unit 150 may calculate a rotation angle of the polarization caused by the measurement object 50 by comparing the detection signals of the reaction light 71 and the reaction light 75. For example, when the reaction light 51 is split into the first reaction light 71 of the first polarization Pb and the second reaction light 75 of the second polarization Pc by the anisotropic meta surface element 70, and the first reaction light 71 and the second reaction light 75 are detected by the first detector 101 and the second detector 103, respectively, the determination unit 150 may compare a first detection signal S1 of the first detector 101 to a second detection signal S2 of the second detector 103 to calculate the rotation angle of the polarization due to the measurement object 50.

The polarimeter according to an example embodiment may split the reaction light 51 of the measurement object 50 into the first reaction light 71 of the first polarization Pb, for example, a horizontal linear polarization and the second reaction light 75 of the second polarization Pc, for example, a vertical linear polarization using the anisotropic meta surface element 70 having a large birefringence, may compare the relative intensities of the first reaction light 71 and the second reaction light 75, and may thereby calculate the rotation angle of the polarization.

According to the polarimeter, the anisotropic meta surface element 70 may be used as a polarization splitter, thereby implementing a small-sized polarimeter having a high sensitivity.

The polarimeter according to an example embodiment may be applied to a glucose analysis and a chemical analysis in food, beverages, and medicine fields. For example, the polarimeter according to an example embodiment may be applied to a small-sized glucose detector having a high sensitivity, etc.

Figure 5:
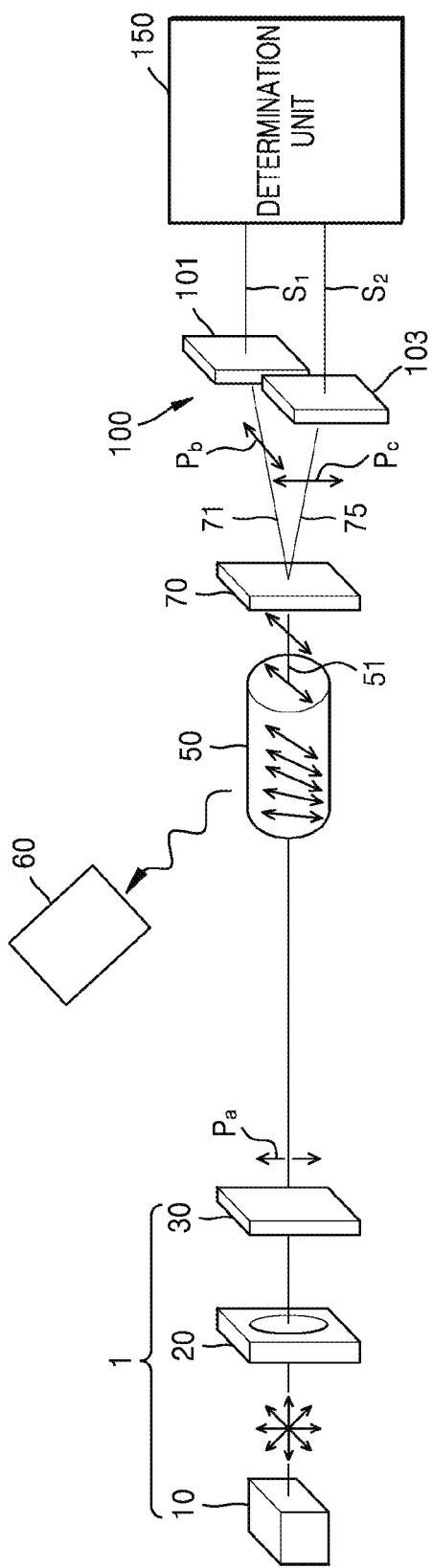
FIGS. 5, 6, and 7 schematically show configurations of polarimeters according to example embodiments.

FIG. 5 schematically shows a configuration of a polarimeter according to another example embodiment. As compared with FIG. 1, there is a difference that the polarimeter of FIG. 5 further includes a spectrometer 60 to detect scattered light such as Raman scattered light from the measurement object 50.

According to the polarimeter according to this example embodiment, by further including the spectrometer 60, an analysis accuracy of the measurement object 50 may be further improved by combining Raman spectroscopic information and polarization rotation information. In the present example embodiment, a Raman spectroscopic signal of the spectrometer 60 may be input to the determination unit 150. The determination unit 150 may combine the Raman spectroscopic information and the polarization rotation information, and thus analysis information of the measurement object 50 may be obtained. As another example, according to the polarimeter according to an example embodiment, a separate processing unit may be further provided to combine the Raman spectroscopic signal input from the spectrometer 60 and the polarization rotation information input from the determination unit 150, and thus the analysis information of the measurement object 50 may be obtained.

FIGS. 1 and 5 show an example in which the detection unit 100 includes a plurality of detectors, for example, the first detector 101 detecting the first reaction light 71 of the first polarization Pb and the second detector 103 detecting the second reaction light 75 of the second polarization Pc, respectively, to detect the reaction light 71 and the reaction light 75. The polarimeter according to an example embodiment may include a single detector 110 or 130 in the detection unit 100, as shown in FIG. 6 and FIG. 7.

Figure 6:
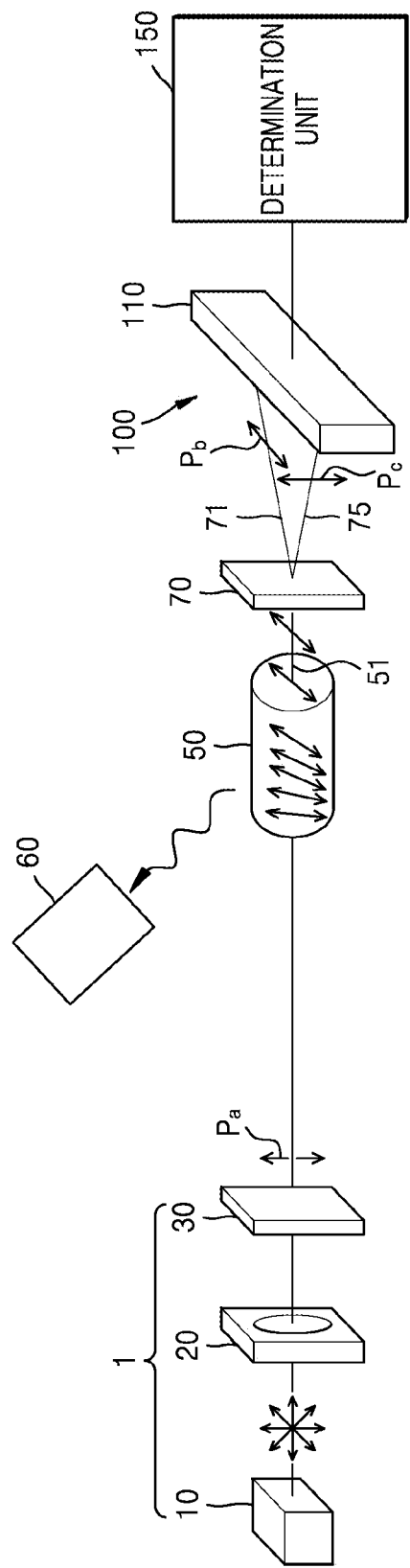

FIG. 6 shows a case in which the detector 100 includes a photodiode linear array as the single detector 110. FIG. 7 shows a case in which the detector 100 includes an image sensor as the single detector 130. FIGS. 6 and 7 illustrate an example in which the spectrometer 60 is additionally provided as shown in FIG. 5. In the case of the example embodiments of FIGS. 6 and 7, a structure excluding the spectrometer 60, as shown in FIG. 1, may be provided.

Figure 7:
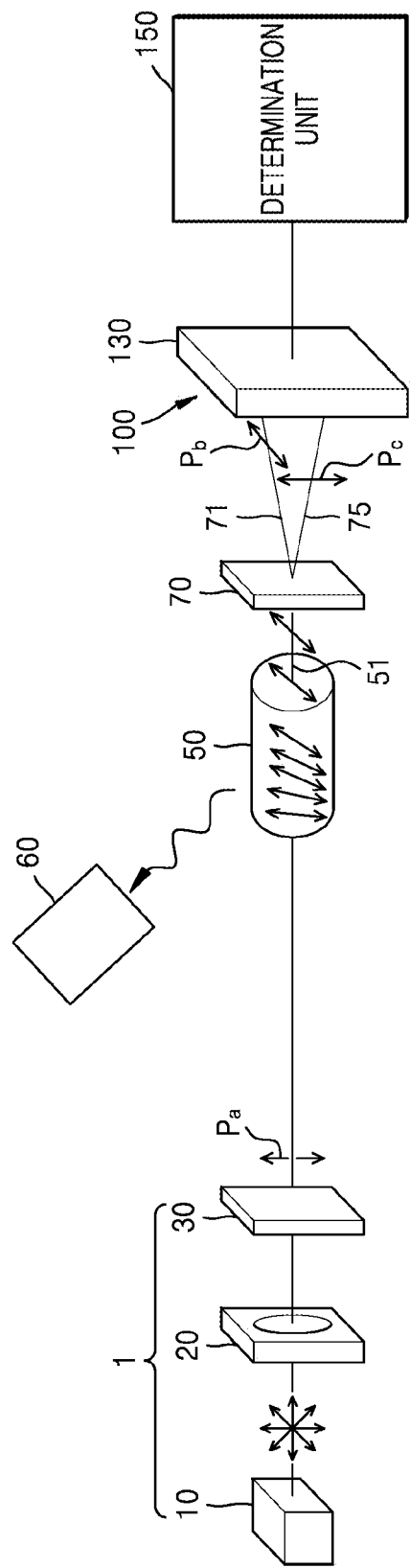

Referring to FIGS. 6 and 7, the detection unit 100 may apply the photodiode linear array or the image sensor as the single detectors 110 and 130 in order to independently detect the reaction light 71 and the reaction light 75 which have been split according to polarization and are incident at different incident angles, for example, the first reaction light 71 of the first polarization Pb and the second reaction light 75 of the second polarization Pc.

When the detection unit 100 includes a single detectors 110 of 130 as shown in FIGS. 6 and 7, the first detection signal S1 of the first reaction light 71 and the second detection signal S2 of the second reaction light 75 detected by the single detectors 110 and 130 are input to the determination unit 150. The determination unit 150 compares the input first detection signal S1 and second detection signal S2 and calculates the rotation angle of the polarization.

Although the anisotropic meta surface element 70 is spaced apart from the detection unit 100 as shown in FIGS. 1 and 5 to 7, the anisotropic meta surface element 70 may be located on a light receiving surface of the detection unit 100. The anisotropic meta surface element 70 may be located on the light receiving surface of the detection unit 100 since no physical distance is required to split the reaction light 51 of the measurement object 50 according to polarization. When the anisotropic meta surface element 70 is disposed on the light receiving surface of the detection unit 100, a polarimeter with a more compact size may be implemented.

According to the polarimeter according to an example embodiment, since an anisotropic meta surface element having a meta surface is applied to a polarization splitter, a small-sized polarimeter having a high rotation angle measurement sensitivity of polarized light passing through an optically active material may be implemented, thereby improving a form factor of the polarimeter.

The polarimeter may be applied to a glucose analysis and a chemical analysis in food, beverage and medicine fields.

It should be understood that example embodiments described herein should be considered in a descriptive sense only and not for purposes of limitation. Descriptions of features or aspects within each example embodiment should typically be considered as available for other similar features or aspects in other example embodiments.

While one or more example embodiments have been described with reference to the figures, it will be understood by those of ordinary skill in the art that various changes in form and details may be made therein without departing from the spirit and scope as defined by the following claims.

What is claimed is:

1. A polarimeter comprising:
   a light source unit configured to irradiate source light onto a measurement object;
   an anisotropic meta surface element disposed to receive reaction light transmitted through the measurement object and configured to split the reaction light, according to polarization, into first reaction light and second reaction light;
   a detection unit configured to detect the first reaction light and the second reaction light; and
   a determination unit configured to calculate a rotation angle of polarization caused by the measurement object by comparing a first detection signal of the first reaction light and a second detection signal of the second reaction light,
   wherein the anisotropic meta surface element comprises a phase mask having a sub wavelength structure,
   wherein the anisotropic meta surface element comprises a low refractive index dielectric substrate and an array of high refractive index dielectric three-dimensional shapes, each having the sub wavelength structure, disposed on the low refractive index dielectric substrate, and
   wherein the anisotropic meta surface element is configured to adjust a reaction to polarization by a size difference between a first axis and a second axis of each of the array of high refractive index dielectric three-dimensional shapes.

2. The polarimeter of claim 1, wherein the first reaction light has a first polarization and the second reaction light has a second polarization, orthogonal to the first polarization.

3. The polarimeter of claim 2, wherein a polarization of the source light is one of the first polarization and the second polarization.

4. The polarimeter of claim 2, wherein the first polarization is a first linear polarization and the second polarization is a second linear polarization, orthogonal to the first linear polarization.

5. The polarimeter of claim 1, wherein the anisotropic meta surface element is disposed on a light-receiving surface of the detection unit.

6. The polarimeter of claim 1, wherein the source light has a specific polarization and the light source unit comprises:
   a light source configured to emit light; and
   a polarizer configured to polarize the light emitted from the light source and thereby emit the source light.

7. The polarimeter of claim 6, wherein the polarizer comprises a meta surface polarizer.

8. The polarimeter of claim 6, wherein the specific polarization is a linear polarization.

9. The polarimeter of claim 1, wherein an output of the meta surface polarizer is determined by a size difference between a first axis and a second axis of each of the array of high refractive index dielectric three-dimensional shapes.

10. The polarimeter of claim 1, wherein the detection unit comprises: a first detector configured to detect the first reaction light and a second detector configured to detect the second reaction light.

11. The polarimeter of claim 10, wherein each of the first detector and the second detector comprises one of a photodiode, a photo multiplier tube detector, a photodiode linear array, and an image sensor.

12. The polarimeter of claim 1, wherein the detection unit comprises a single detector,
   wherein the single detector comprises: one of a photodiode linear array and an image sensor.

13. The polarimeter of claim 1, further comprising: a spectrometer configured to measure light scattered from the measurement object.

14. The polarimeter of claim 1, wherein the measurement object comprises an optically active material.

15. The polarimeter of claim 1, wherein the array of high refractive index dielectric three-dimensional shapes comprises an array of high refractive index dielectric three-dimensional elliptical posts.

16. A polarimeter comprising:
   a light source which outputs light only onto a measurement object;
   an anisotropic meta surface element, positioned to receive reaction light transmitted through the measurement object, which separates the reaction light into first reaction light having a first polarization and second reaction light having a second polarization, orthogonal to the first polarization;
   detection unit comprising at least one detector which detects the first reaction light and thereby outputs a first detection signal and which detects the second reaction light and thereby outputs a second detection signal; and
   a determination unit comprising a memory and a processor configured to execute software instructions stored in the memory and thereby compare the first detection signal with the second detection signal, and calculate a rotation of polarization caused by transmission through the measurement object,
   wherein the anisotropic meta surface element comprises a phase mask having a sub wavelength structure,
   wherein the anisotropic meta surface element comprises a low refractive index dielectric substrate and an array of high refractive index dielectric three-dimensional shapes, each having the sub wavelength structure, disposed on the low refractive index dielectric substrate, and wherein the anisotropic meta surface element is configured to adjust a reaction to polarization by a size difference between a first axis and a second axis of each of the array of high refractive index dielectric three-dimensional shapes.

17. The polarimeter of claim 16, wherein the measurement object comprises an optically active material.

18. The polarimeter of claim 16, wherein the array of high refractive index dielectric three-dimensional shapes comprises an array of high refractive index dielectric three-dimensional elliptical posts.

* * * * *